(12) United States Patent
Zimmerman (10) Patent No.: US 11,471,652 B2
(45) Date of Patent: Oct. 18, 2022

(54) APPARATUS, SYSTEM, AND METHOD FOR EXTENDING A GUIDEWIRE

(71) Applicant: Lake Region Manufacturing, Inc., Chaska, MN (US)

(72) Inventor: John Matthew Zimmerman, Minnetrista, MN (US)

(73) Assignee: Lake Region Manufacturing, Inc., Chaska, MN (US)

(*) Notice: Subject to any disclaimer, the term of this patent is extended or adjusted under 35 U.S.C. 154(b) by 609 days.

(21) Appl. No.: 15/884,429

(22) Filed: Jan. 31, 2018

(65) Prior Publication Data

US 2019/0232026 A1   Aug. 1, 2019

(51) Int. Cl.
*A61M 25/09* (2006.01)
*A61M 25/00* (2006.01)

(52) U.S. Cl.
CPC .. *A61M 25/0905* (2013.01); *A61M 25/09041* (2013.01); *A61M 25/002* (2013.01)

(58) Field of Classification Search
None
See application file for complete search history.

(56) References Cited

U.S. PATENT DOCUMENTS

| | | | |
|---|---|---|---|
| 4,907,332 A * | 3/1990 | Christian | A61M 25/09 29/237 |
| 5,113,872 A | 5/1992 | Jahrmarkt et al. | |
| 5,139,032 A * | 8/1992 | Jahrmarkt | A61M 25/0905 600/434 |
| 5,191,888 A | 3/1993 | Palmer et al. | |
| 5,234,002 A | 8/1993 | Chan et al. | |
| 5,320,613 A * | 6/1994 | Houge | A61M 25/00 604/256 |
| 5,338,301 A | 8/1994 | Diaz et al. | |
| 5,409,459 A | 4/1995 | Gambale | |
| 5,484,419 A * | 1/1996 | Fleck | A61M 25/0113 604/171 |
| 5,546,958 A * | 8/1996 | Thorud | A61M 25/0905 600/434 |

(Continued)

FOREIGN PATENT DOCUMENTS

| | | |
|---|---|---|
| EP | 1253962 | 11/2002 |
| WO | 9305841 | 4/1993 |
| WO | 2008115136 | 9/2008 |

*Primary Examiner* — Alex M Valvis
*Assistant Examiner* — Aurelie H Tu
(74) *Attorney, Agent, or Firm* — Michael F. Scalise (57) ABSTRACT

In various examples, an apparatus facilitates attachment of an extension wire to a guidewire. The apparatus includes a body portion including a lumen sized to accommodate a distal end of the extension wire therein. A cutout is defined within a portion of a sidewall of the body portion, the cutout allowing access to the lumen. A funnel portion is disposed within a distal end of the body portion and includes an opening in the distal end of the body portion. The funnel portion includes a tapered wall converging from the opening to the lumen, wherein, with the distal end of the extension wire disposed within the lumen, the funnel portion facilitates alignment and attachment of a proximal end of the guidewire with the distal end of the extension wire. In other examples, a system or a method facilitates attachment of an extension wire to a guidewire.

20 Claims, 7 Drawing Sheets

(56) References Cited

U.S. PATENT DOCUMENTS

| | | | |
|---|---|---|---|
| 5,617,875 A | 4/1997 | Schwager | |
| 6,248,082 B1 | 6/2001 | Jafari et al. | |
| 7,513,878 B2 | 4/2009 | Hamilton et al. | |
| 8,231,550 B2 | 7/2012 | Teirstein et al. | |
| 8,850,676 B2 | 10/2014 | Schmitt | |
| 2001/0016712 A1* | 8/2001 | Hamilton | A61M 25/0113 604/170.01 |
| 2003/0036712 A1* | 2/2003 | Heh | A61M 25/09041 600/585 |
| 2003/0114775 A1* | 6/2003 | Ehr | A61M 25/0905 600/585 |
| 2003/0225397 A1 | 12/2003 | Baechtold et al. | |
| 2004/0059369 A1 | 3/2004 | Duffy et al. | |
| 2004/0073193 A1 | 4/2004 | Houser et al. | |
| 2006/0142703 A1 | 6/2006 | Carter et al. | |
| 2008/0082051 A1 | 4/2008 | Miller et al. | |
| 2012/0179140 A1* | 7/2012 | Fojtik | A61M 25/0905 604/528 |
| 2012/0210569 A1* | 8/2012 | Schmitt | A61M 25/09041 29/700 |
| 2014/0237798 A1 | 8/2014 | Cude et al. | |
| 2014/0276436 A1* | 9/2014 | Lafitte | A61M 25/0662 604/164.13 |
| 2016/0096005 A1* | 4/2016 | Bhola | A61B 1/00165 600/424 |

\* cited by examiner

APPARATUS, SYSTEM, AND METHOD FOR EXTENDING A GUIDEWIRE

BACKGROUND

The present invention relates to extending a guidewire, and more specifically relates to an apparatus, system, and method for facilitating attachment of an extension wire onto a guidewire.

A guidewire is often used within a patient to serve as a guide for placement of a larger device, such as a catheter, for instance. In some instances, a procedure may require one device to be removed and replaced with another device, such as, for instance, swapping one catheter for another. In such a situation, it is often recommended to attach an extension wire to an end of the guidewire extending out from the patient in order to enable the guidewire to be held in place during removal of the first device and insertion of the second device.

With many guidewires and other working wires being relatively small in diameter, in some cases as small as 0.006 inches in diameter, it can oftentimes be difficult to attach an extension wire, which can include a hypotube attachment having an opening as small as 0.010 inches into which an end of the guidewire or other working wire is to be fed. Couple this with potentially low light conditions and/or body fluids being present, and the difficulty, time, and dexterity of attaching an extension wire to a guidewire or other working wire increases.

OVERVIEW

This overview is intended to provide an overview of subject matter of the present patent document. It is not intended to provide an exclusive or exhaustive explanation of the invention. The detailed description is included to provide further information about the present patent document.

The present inventor has recognized, among other things, that the present subject matter can be used with respect to the extension of a guidewire or other working wire. In various examples, the apparatus, system, and method can facilitate the attachment of an extension wire to a guidewire or other working wire. The present inventor has recognized the present subject matter can be used to decrease time and difficulty involved with the attachment of an extension wire to a guidewire or other working wire during a procedure. To better illustrate the apparatuses, systems, and methods described herein, a non-limiting list of examples is provided here:

Example 1 can include subject matter that can include an apparatus for facilitating attachment of an extension wire to a guidewire. The apparatus includes a body portion including a sidewall and a lumen through the body portion. The lumen is sized to accommodate a distal end of the extension wire therein. A cutout is defined within a portion of the sidewall. The cutout extends through the sidewall from an exterior of the body portion to the lumen. The cutout allows access to the lumen. A funnel portion is disposed within a distal end of the body portion. The funnel portion includes an opening in the distal end of the body portion. The opening includes an opening diameter larger than a lumen diameter of the lumen. The funnel portion includes a tapered wall converging from the opening to the lumen, wherein, with the distal end of the extension wire disposed within the lumen, the funnel portion facilitates alignment and attachment of a proximal end of the guidewire with the distal end of the extension wire.

In Example 2, the subject matter of Example 1 is optionally configured such that the lumen is disposed along a longitudinal axis of the body portion.

In Example 3, the subject matter of any one of Examples 1 and 2 optionally includes an attachment portion disposed at a proximal end of the body portion. The attachment portion is configured for attachment to an extension holder. The extension holder is configured to house the extension wire within the extension holder prior to attachment to and use with the guidewire.

In Example 4, the subject matter of any one of Examples 1-3 is optionally configured such that, with the distal end of the extension wire disposed within the lumen of the body portion, a portion of the extension wire within the cutout is exposed. The cutout is sized to allow a user to contact the exposed portion of the extension wire to inhibit the extension wire from moving relative to the body portion during attachment of the extension wire to the guidewire.

In Example 5, the subject matter of any one of Examples 1-4 is optionally configured such that the funnel portion is configured to direct the proximal end of the guidewire toward a hypotube disposed at the distal end of the extension wire to facilitate attachment of the proximal end of the guidewire within the hypotube.

In Example 6, the subject matter of Example 1 is optionally configured such that the hypotube is configured to frictionally engage with the proximal end of the guidewire.

In Example 7, the subject matter of any one of Examples 1-6 optionally includes an anti-migration feature configured to inhibit movement of the extension wire with respect to the apparatus.

In Example 8, the subject matter of Example 7 is optionally configured such that the anti-migration feature includes a resilient member at least partially disposed within a portion of the lumen of the body portion, wherein, with at least a portion of the extension wire being disposed within the lumen, the resilient member contacts the extension wire to inhibit movement of the extension wire with respect to the apparatus.

In Example 9, the subject matter of Example 8 is optionally configured such that the anti-migration feature includes a passage within the body portion. The passage intersects with the lumen. The resilient member is positioned within the passage and into the lumen to contact the extension wire.

Example 10 can include, or can optionally be combined with any one of Examples 1-9 to include subject matter that can include a guidewire extension kit for facilitating attachment of an extension wire to a proximal end of a guidewire. The kit includes an elongate extension wire configured to be attached to the proximal end of the guidewire. An extension holder includes an elongate interior. The extension holder is configured to house the extension wire within the interior of the extension holder prior to attachment to and use with the guidewire. An alignment device includes a body portion including a sidewall and a lumen through the body portion. The lumen is sized to accommodate the distal end of the extension wire therein. A cutout is defined within a portion of the sidewall. The cutout extends through the sidewall from an exterior of the body portion to the lumen. The cutout allows access to the lumen. A funnel portion is disposed within a distal end of the body portion. The funnel portion includes an opening in the distal end of the body portion. The opening includes an opening diameter larger than a lumen diameter of the lumen. The funnel portion includes a tapered wall converging from the opening to the lumen, wherein, with the distal end of the extension wire disposed within the lumen, the funnel portion facilitates alignment and attachment of the proximal end of the guidewire with the distal end of the extension wire.

In Example 11, the subject matter of Example 10 is optionally configured such that the lumen is disposed along a longitudinal axis of the body portion.

In Example 12, the subject matter of any one of Examples 10 and 11 is optionally configured such that the body portion includes an attachment portion disposed at a proximal end of the body portion. The attachment portion is configured for attachment to the extension holder.

In Example 13, the subject matter of any one of Examples 10-12 is optionally configured such that, with the distal end of the extension wire disposed within the lumen of the body portion, a portion of the extension wire within the cutout is exposed. The cutout is sized to allow a user to contact the exposed portion of the extension wire to inhibit the extension wire from moving relative to the body portion during attachment of the extension wire to the guidewire wire.

In Example 14, the subject matter of any one of Examples 10-13 is optionally configured such that the extension wire includes a hypotube disposed at the distal end of the extension wire. The hypotube includes a lumen sized to accept the proximal end of the guidewire to attach the extension wire to the guidewire.

In Example 15, the subject matter of Example 14 is optionally configured such that the hypotube is configured to frictionally engage with the proximal end of the guidewire.

In Example 16, the subject matter of any one of Examples 10-15 is optionally configured such that the alignment device includes an anti-migration feature to inhibit movement of the elongate extension wire with respect to the alignment device.

In Example 17, the subject matter of Example 16 is optionally configured such that the anti-migration feature includes a resilient member at least partially disposed within a portion of the lumen of the body portion, wherein, with at least a portion of the extension wire being disposed within the lumen, the resilient member contacts the extension wire to inhibit movement of the extension wire with respect to the alignment device.

In Example 18, the subject matter of Example 17 is optionally configured such that the anti-migration feature includes a passage within the body portion. The passage intersects with the lumen. The resilient member is positioned within the passage and into the lumen to contact the extension wire.

Example 19 can include, or can optionally be combined with any one of Examples 1-18 to include subject matter that can include a method of extending a guidewire. A guidewire extension kit is selected for use in extending the guidewire. The guidewire extension kit includes an elongate extension wire configured to be attached to a proximal end of the guidewire. An extension holder includes an elongate interior. The extension holder is configured to house the extension wire within the interior of the extension holder prior to attachment to and use with the guidewire. An alignment device includes a body portion including a sidewall and a lumen through the body portion. The lumen is sized to accommodate a distal end of the extension wire therein. A cutout is defined within a portion of the sidewall. The cutout extends through the sidewall from an exterior of the body portion to the lumen. The cutout allows access to the lumen. A funnel portion is disposed within a distal end of the body portion. The funnel portion includes an opening in the distal end of the body portion. The opening includes an opening diameter larger than a lumen diameter of the lumen. The funnel portion includes a tapered wall converging from the opening to the lumen, wherein, with the distal end of the extension wire disposed within the lumen, the funnel portion facilitates alignment and attachment of the proximal end of the guidewire with the distal end of the extension wire. The alignment device of the guidewire extension kit is placed proximate to the proximal end of the guidewire to be extended. A force is exerted on a portion of the extension wire within a portion of the lumen exposed by the cutout to press the extension wire against the body portion of the alignment device to inhibit relative motion between the body portion of the alignment device and the extension wire. The alignment device is moved toward the proximal end of the guidewire so that the proximal end of the guidewire enters the funnel portion of the alignment device, becomes aligned with the distal end of the extension wire, and attaches to the distal end of the extension wire. The force on the portion of the extension wire within the portion of the lumen exposed by the cutout is released to allow relative motion between the body portion of the alignment device and the extension wire. The alignment device is pulled proximally with respect to the guidewire to allow the extension wire to exit from the extension holder and the distal end of the body portion of the alignment device, leaving the extension wire connected to the guidewire, thereby extending the guidewire.

In Example 20, the subject matter of Example 19 is optionally configured such that exerting the force on the portion of the extension wire within the portion of the lumen exposed by the cutout includes placing one or more digits within the cutout of the alignment device to make contact with the portion of the extension wire within the portion of the lumen exposed by the cutout.

DETAILED DESCRIPTION

The present patent application relates to an apparatus, system, and method for facilitating the attachment of an extension wire to a guidewire or other working wire. Other such working wires can include a diagnostic wire, for instance. Guidewires and other such working wires are typically used to navigate to a desired location within a patient. Once in place, a catheter or other device can be introduced over the guidewire or other such working wire to the desired location. In some procedures, it may become necessary to remove a first catheter or other device from within the patient and replace it with a second catheter or other device. While removing the first device and inserting the second device, it is oftentimes important to keep the guidewire or other working wire stationary so as to not migrate to a location other than the desired location. In some instances, it is necessary to extend the guidewire or other working wire in order to maintain access to the guidewire or other working wire during the exchange to restrain and inhibit movement of the guidewire or other working wire, thereby maintaining the position of the guidewire or other working wire at the desired location. In order to extend the guidewire or other working wire, an extension wire can be attached to the exposed proximal end of the guidewire or other working wire. Due to the relatively small sizes of the diameter of the guidewire or other working wire, as well as the potentially low-light conditions and possible presence of body fluids, attachment of an extension wire to a guidewire or other working wire can often be a difficult and time-consuming process. The various examples presented herein seek to facilitate the attachment of an extension wire to a guidewire or other working wire.

Figures 2A, 2B, 2C, 2D:
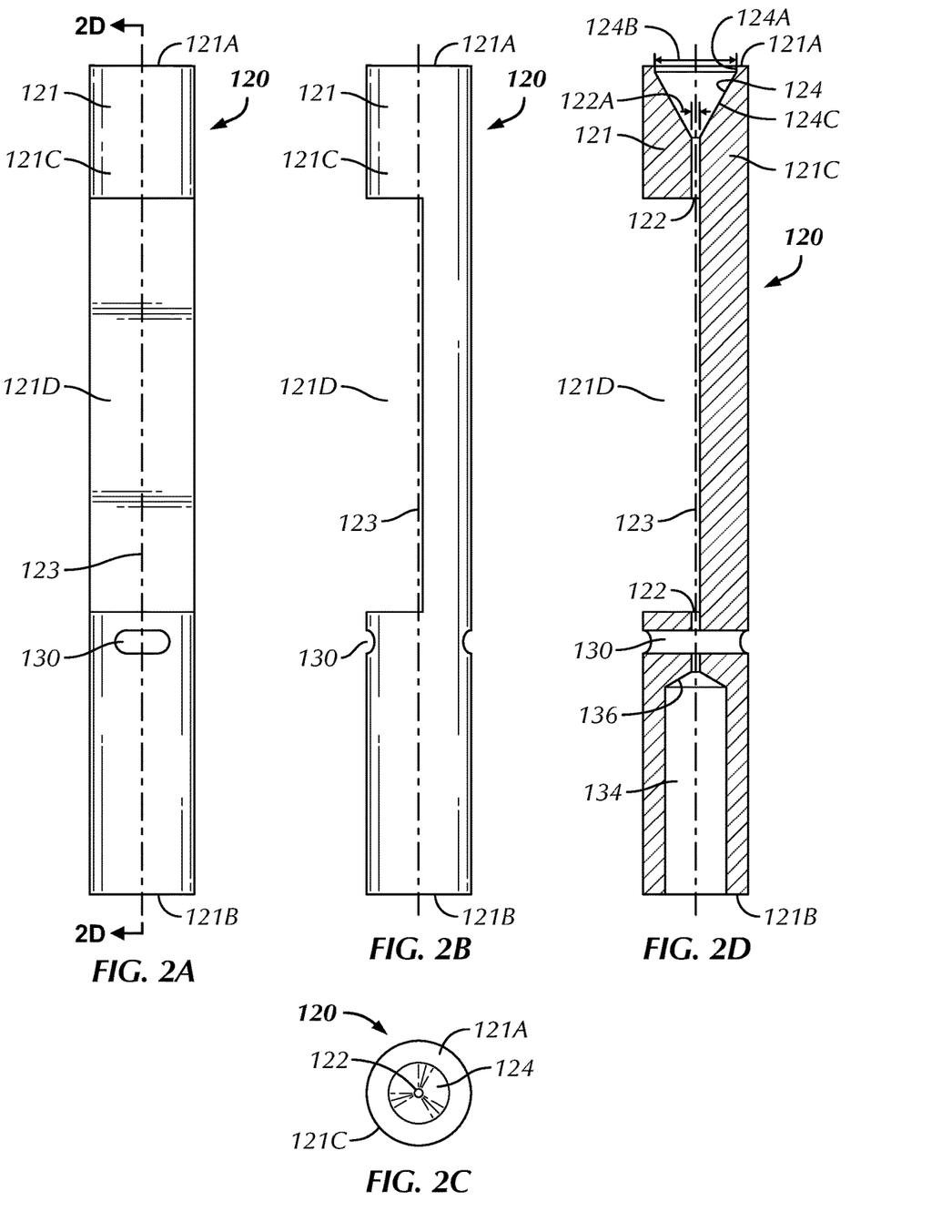
FIG. 2A is a top view of an alignment device in accordance with at least one example of the invention.
FIG. 2B is a side view of an alignment device in accordance with at least one example of the invention.
FIG. 2C is an end view of an alignment device in accordance with at least one example of the invention.
FIG. 2D is a cross-sectional view of the alignment device of FIG. 2A taken along line 2D-2D.
Figure 3A:
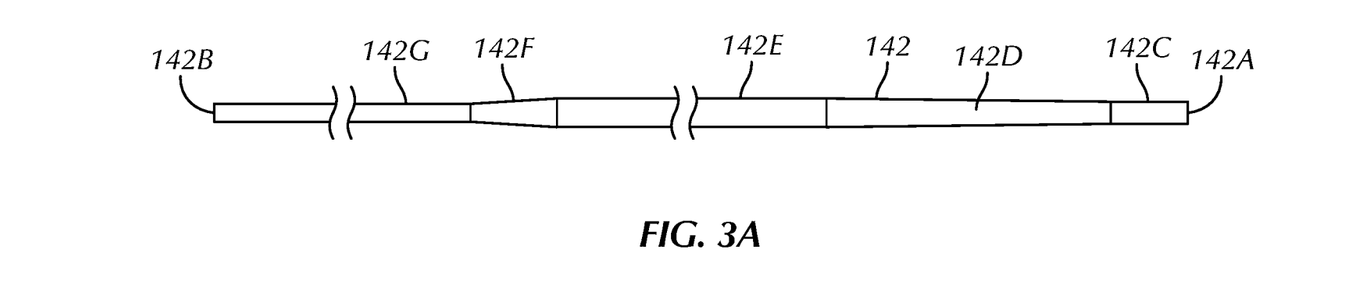
FIG. 3A is a side view of a core for an extension wire in accordance with at least one example of the invention.
Figure 3B:
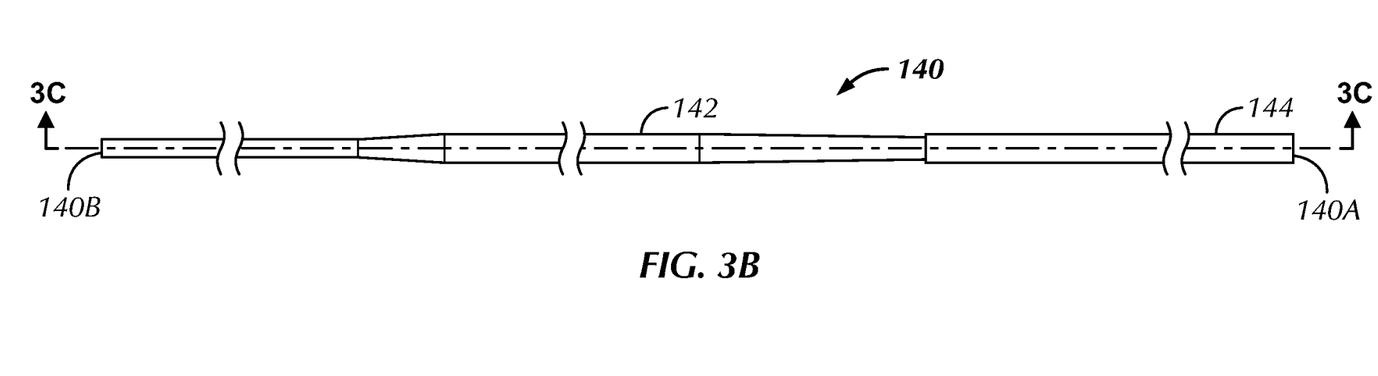
FIG. 3B is a side view of an extension wire in accordance with at least one example of the invention.
Figure 3C:
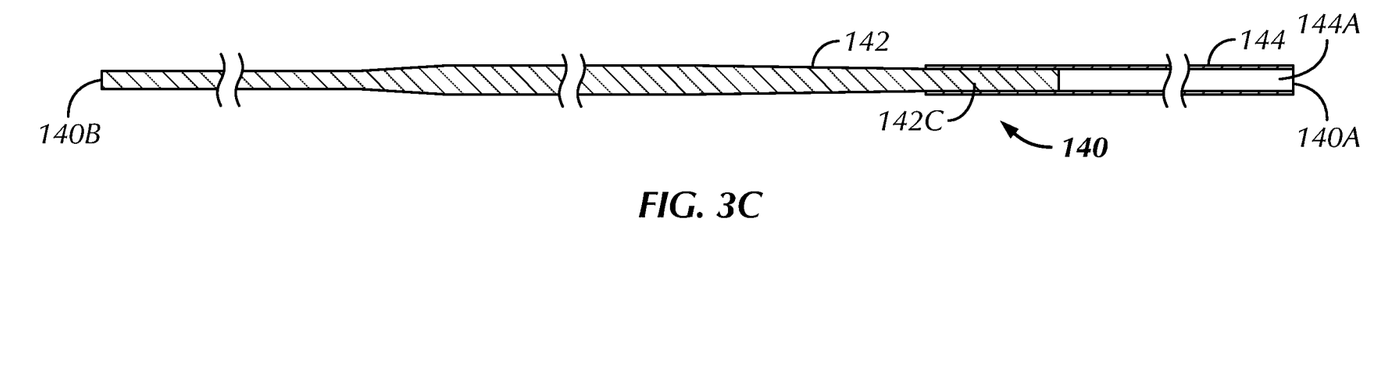
FIG. 3C is a cross-sectional view of the extension wire of FIG. 3A taken along line 3C-3C.
Figure 4:
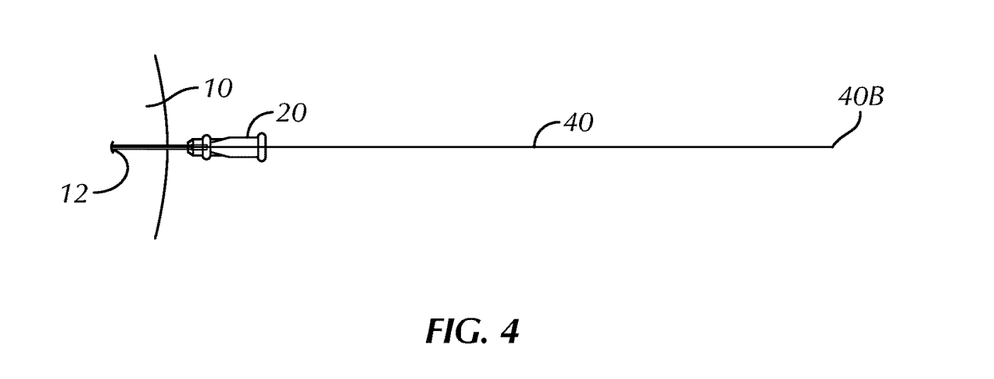
FIG. 4 shows a proximal end of a guidewire extending from an introducer within a patient.

Referring to FIGS. 1A-3C, in some examples, a guidewire extension kit 100 can be used to facilitate attachment of an extension wire 140 to a proximal end 40B of a guidewire or other working wire 40 (see FIG. 4). In some examples, the kit 100 includes the elongate extension wire 140 configured to be attached to the proximal end 40B of the guidewire 40. In some examples, the extension wire 140 includes a distal end 140A and a proximal end 140B, wherein the distal end 140A of the extension wire 140 is configured to be attached to the proximal end 40B of the guidewire 40. In various examples, the guidewire 40 can include various types of working wires, including, but not limited to, a guidewire, a diagnostic wire, or an other elongate member configured to be inserted within a patient. In various examples, the extension wire 140 can be configured to be used with any elongate working wire insertable within a patient for which a catheter exchange or other such procedure may be desirable.

Referring briefly to FIGS. 3A-3C, in some examples, the extension wire 140 includes an elongate shaft 142, having a distal end 142A and a proximal end 142B, and a connection member 144 disposed at the distal end 142A of the shaft 142. In various examples, the shaft 142 can include a solid core or a hollow core, depending upon the application of the shaft 142. For instance, if a wire, a fiber, a fluid, or the like is to be passed within the shaft 142, the shaft 142 can include a hollow core. In various examples, a length of the shaft 142 depends upon the length of catheter that is to be exchanged. For instance, a longer shaft 142 can be used with a longer catheter to be exchanged. In some examples, the length of the shaft 142 of the extension wire 140 should be slightly longer than the catheter to be exchanged to enable a physician or other user to hold either the guidewire 40 or the extension wire 140 throughout the catheter exchange in order to keep the guidewire 40 and the extension wire 140 stationary with respect to the patient during the catheter exchange.

In some examples, the shaft 142 can include differing diameters along the length of the shaft 142. For instance, in some examples, the shaft 142 can include a narrowed distal portion 142C and an expanding tapered portion 142D extending proximally from the narrowed distal portion 142C. In some examples, the expanding tapered portion 142D expands to a diameter of an expanded portion 142E immediately proximal from the narrowed distal portion 142C. The expanded portion 142E, in some examples, has a diameter substantially equal to a diameter of the guidewire 40. In other examples, however, the expanded portion 142E need not have a diameter substantially equal to the diameter of the guidewire 40, such that the diameter of the expanded portion 142E can be larger or smaller than the diameter of the guidewire 40. For instance, in some examples, the diameter of the expanded portion 142E can be selected according to achieve a particular stiffness or other characteristic of the shaft 142. In some examples, the shaft 142 includes a narrowing tapered portion 142F proximal of the expanded portion 142E. The narrowing tapered portion 142F, in some examples, tapers down to a diameter of a narrowed proximal portion 142G, which is proximal of the narrowing tapered portion 142F. In some examples, the narrowed proximal portion 142G includes a relatively small diameter compared to an inside diameter of a catheter, for instance, to facilitate insertion of the shaft 142 into the catheter during a catheter exchange. Although such a configuration of the shaft 142 is shown and described herein, the shaft 142 is merely exemplary and is not intended to be limiting. That is, the shaft, in other examples, can include other geometries, for instance, to work with working wires of various configurations and/or perform properly in catheter exchange procedures or other procedures for which an extension wire is desirable.

In some examples, the connection member 144 is configured to engage with the proximal end 40B of the guidewire 40. The connection member 144 can take various forms depending upon the guidewire 40 to which the connection member 144 is to be engaged. In some examples, such as the example shown in FIGS. 3B and 3C, the connection member 144 includes a hypotube 144 sized and shaped to be attached to the narrowed distal portion 142C of the shaft 142 and, in turn, to be selectively engaged to the proximal end 40B of the guidewire 40. In some examples, the hypotube 144 is disposed at the distal end of the extension wire 140 and includes a lumen 144A sized to accept the proximal end 40B of the guidewire 40 to attach the extension wire 140 to the guidewire 40. The narrowed distal portion 142C of the shaft 142, in some examples, is configured to fit within the lumen 144A of the hypotube 144. In some examples, the narrowed distal portion 142C is engaged within the lumen 144A using, for instance, a friction fit, by welding, by soldering, or using an adhesive. In some examples, the lumen 144A of the hypotube 144 is only partially filled by the narrowed distal portion 142C of the shaft 142 in order to leave a length of the lumen 144A free to accept the proximal end 40B of the guidewire 40.

In some examples, the lumen 144A of the hypotube 144 is sized to accept and releasably retain the proximal end 40B of the guidewire 40 within the lumen 144A. The hypotube 144, in some examples, is configured to frictionally engage with the proximal end 40B of the guidewire 40. In some examples, the inside diameter of the lumen 144A is slightly larger than a diameter of the proximal end 40B of the guidewire 40 and the proximal end 40B of the guidewire is formed to include a slightly curved or wavy shape, such that insertion of the proximal end 40B of the guidewire 40 into the lumen 144A of the hypotube 144 compresses the slightly curved or wavy shape of the proximal end 40B of the guidewire 40. In this way, the compressed proximal end 40B of the guidewire 40 pushes against an inner surface of the lumen 144A to create a retention force and retain the proximal end 40B of the guidewire 40 within the lumen 144A of the hypotube 144. In some examples, this retention force maintains connection of the extension wire 140 to the guidewire 40, thereby allowing a catheter exchange (or other such procedure) to occur. Once the catheter exchange or other procedure is complete, in some examples, the extension wire 140 can be disconnected from the guidewire 40 by pulling the extension wire 140 distally while maintaining the guidewire substantially stationary. In some examples, pulling on the extension wire 140 with sufficient force overcomes the retention force caused by the compressed proximal end 40B of the guidewire 40 and allows the proximal end 40B of the guidewire 40 to be removed from within the lumen 144A of the hypotube 144.

In other examples, the connection member 144 can include a configuration other than the hypotube 144 in order to accommodate a differently configured guidewire. For instance, in some examples, the connection member and the guidewire can include complementary threads, such that the proximal end of the guidewire can be threadably engaged with the connection member to join the extension wire to the guidewire. In other examples, the proximal end of the guidewire can be formed into a shape to facilitate releasable engagement with the connection member, such as, but not limited to an expanding tapered shape, a ridged shaft, or the like. In other examples, one or both of the proximal end of the guidewire and the connection member can include a resilient coating or other material adhered thereto to allow for compression of the resilient material with connection of the extension wire to the guidewire to create a retention force to maintain connection of the guidewire and the extension wire.

Figure 1A:
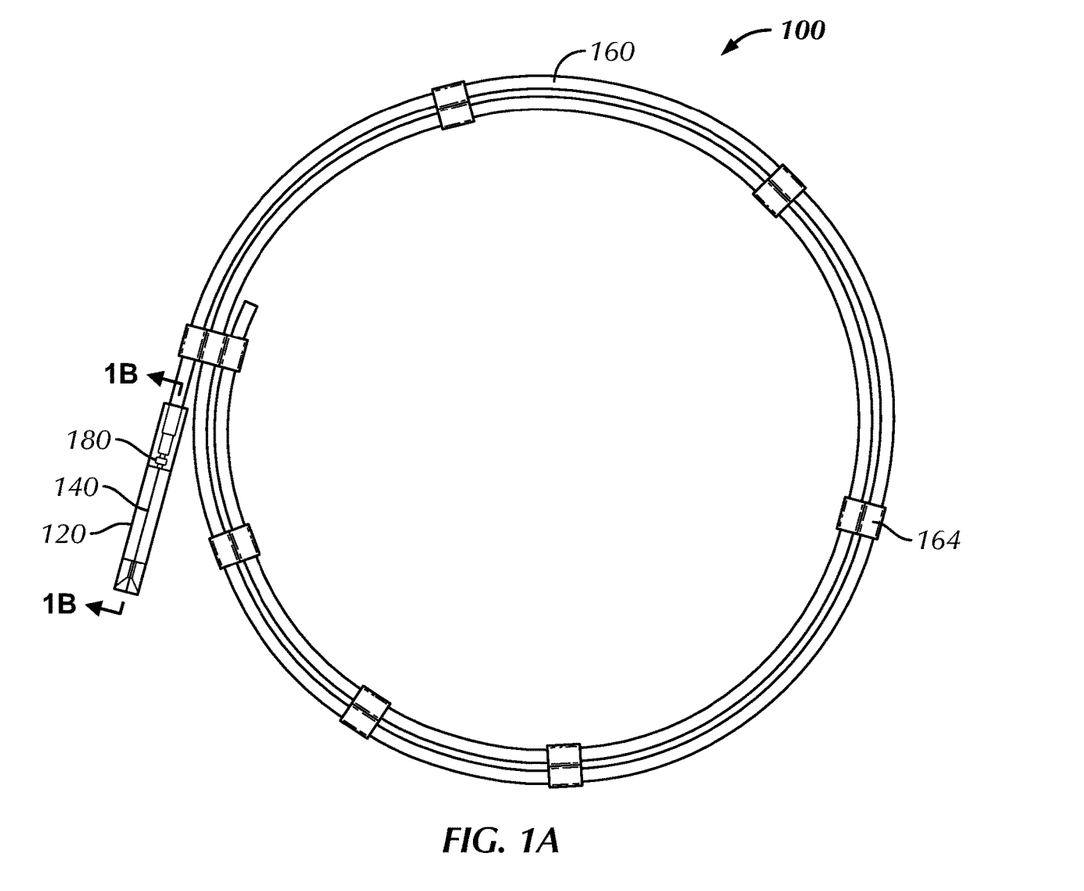
FIG. 1A is a top view of a guidewire extension kit in accordance with at least one example of the invention.
Figure 1B:
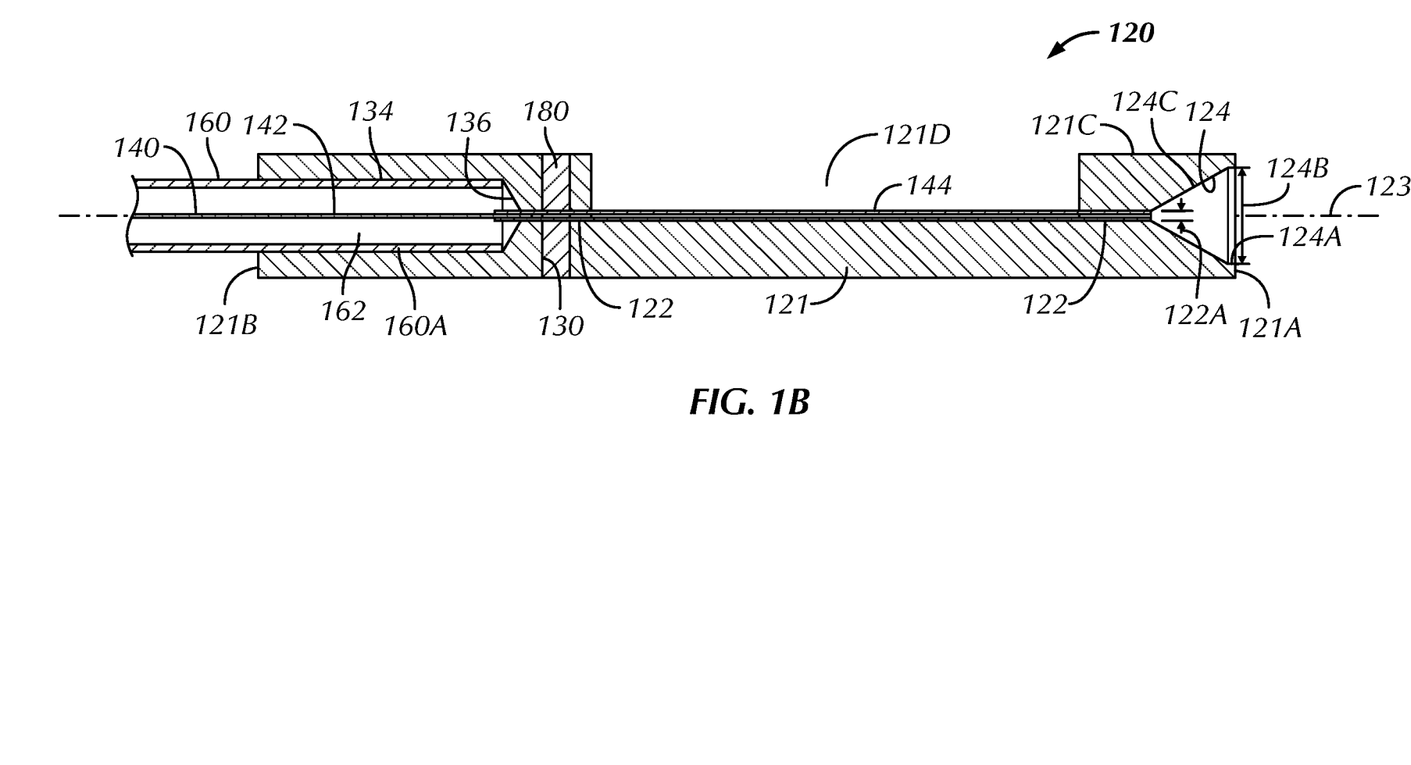
FIG. 1B is a cross-sectional view of a distal end of the guidewire extension kit of FIG. 1A taken along line 1B-1B.

Referring to FIGS. 1A and 1B, in some examples, the kit 100 includes an extension holder 160 including an elongate interior 162. In some examples, the extension holder 160 is configured to house the extension wire 140 within the interior 162 of the extension holder 160 prior to attachment to and use with the guidewire 40. In some examples, the extension holder 160 is tubular and of a length sufficient to house the length of the extension wire 140 within the interior 162 of the extension holder 160. In some examples, the extension holder 160 is spirally curved or looped and held in place with clips 164 to facilitate handling and storage of the kit 100. However, in other examples, the extension holder 160 can be maintained in other configurations, such as a straight configuration, for instance.

Referring now to FIGS. 1A-2C, the kit 100 further includes an alignment device 120. In some examples, the alignment device 120 includes a body portion 121 extending from a distal end 121A to a proximal end 121B and including a sidewall 121C and a lumen 122 through the body portion 121. In some examples, the lumen 122 is sized to accommodate the distal end 140A of the extension wire 140 therein. In further examples, the lumen 122 is sized to accommodate the connection member 144 within the lumen 122. In some examples, the lumen 122 is disposed along a longitudinal axis 123 of the body portion 121. In some examples, the alignment device 120 can be formed from one or more of polyetheretherketone (PEEK), low density polyethylene (LDPE), polycarbonate, or the like.

In some examples, the alignment device 120 includes a cutout 121D defined within a portion of the sidewall 121C, the cutout 121D extending through the sidewall 121C from an exterior of the body portion 121 to the lumen 122. In this way, the cutout 121D allows access to the lumen 122. In some examples, such as is seen in FIG. 1B, the extension wire 140 is accessible within the cutout 121D. In some examples, the lumen 122 is disposed on either side of the cutout 121D. In some examples, the lumen 122 includes a channel disposed along the body portion 121 within which the extension wire 140 can be disposed. In some examples, with the distal end of the extension wire 140 disposed within the lumen 122 of the body portion 121, a portion of the extension wire 140 within the cutout 121D is exposed. In some examples, the cutout 121D is sized to allow a user to contact the exposed portion of the extension wire 140 to inhibit the extension wire 140 from moving relative to the body portion 121 during attachment of the extension wire 140 to the guidewire wire 40B.

In some examples, the alignment device 120 includes a funnel portion 124 disposed within the distal end 121A of the body portion 121. In some examples, the funnel portion 124 includes an opening 124A in the distal end 121A of the body portion 121. In some examples, the opening 124A includes an opening diameter 124B larger than a lumen diameter 122A of the lumen 122. In some examples, the funnel portion 124 includes a tapered wall 124C converging from the opening 124A to the lumen 122, such that, with the distal end 140A of the extension wire disposed within the lumen 122, the funnel portion 124 facilitates alignment and attachment of the proximal end 40B of the guidewire 40 with the distal end 140A of the extension wire 40. That is, a user can use the alignment device 120 to help guide the distal end 140A of the extension wire 140 into alignment with the proximal end 40B of the guidewire 40 by moving the alignment device 120 toward the proximal end 40B of the guidewire 40 such that the proximal end 40B of the guidewire 40 enters the opening 124A and is guided toward the lumen 122 (and the connection member 144 of the extension wire 140 within the lumen 122) by the tapered wall 124C. With continued movement of the alignment device 120 (and the connection member 144 of the extension wire 140 within the alignment device 120) toward the proximal end 40B of the guidewire 40, the guidewire 40 eventually becomes disposed within the lumen 122 and within the connection member 144 of the extension wire 140. In some examples, the user can exert pressure against the extension wire 140 (for instance, by pressing a thumb or other digit against the extension wire 140) within the cutout 121D, essentially pushing the extension wire 140 against the sidewall 121C of the body portion 121 of the alignment device 120, to substantially inhibit movement of the extension wire 140 relative to the alignment device 120 during attachment of the connection member 144 of the extension wire 140 to the proximal end 40B of the guidewire 40. In this way, in some examples, the proximal end 40B of the guidewire 40 can be attached to the connection member 144 of the extension wire 140 without the extension wire 140 being pushed proximally with respect to the alignment device 120.

In some examples, the body portion 121 includes an attachment portion 134 disposed at or within the proximal end 121B of the body portion 121, wherein the attachment portion 134 is configured for attachment to the extension holder 160. That is, in some examples, a distal portion 160A of the extension holder 160 is sized to fit within the attachment portion 134 to couple the extension holder 160 with the alignment device 120. In some examples, the distal portion 160A is sized to frictionally engage within the attachment portion 134. In other examples, the distal portion 160A can be attached to the alignment device 120 in other ways, including, but not limited to, using an adhesive between the distal portion 160A and the attachment portion 134, threadably coupling the attachment portion 134 to the distal portion 160A, using a protrusion-and-recess snapping coupling, using a tab-in-slot (for instance, bayonet-like) coupling, or the like.

In some examples, a distal side of the attachment portion 134 includes a funnel 136 to facilitate insertion of the extension wire 140 within the alignment device 120. In some examples, the funnel 136 can assist in directing the extension wire 140 into the lumen 122 of the body portion 121, for instance, in order to dispose the connection member 144 within the lumen 122 to make the kit 100 ready for use with the guidewire 40 to extend the guidewire 40.

In some examples, the alignment device 120 includes an anti-migration feature 180 to inhibit movement of the elongate extension wire 140 with respect to the alignment device 120. In some examples, the anti-migration feature 180 is meant to limit incidental movement of the extension wire 140 within the alignment device 120 and the extension holder 160. For instance, in some examples, the anti-migration feature 180 is intended to limit movement of the extension wire 140 during shipping, transportation, or other movement of the kit 100. In some examples, the anti-migration feature 180 is not intended to inhibit movement of the extension wire 140 during attachment of the extension wire 140 to the proximal end 40B of the guidewire 40. As described herein, in some examples, placement of a thumb or other digit within the cutout 121D against the extension wire 140, or otherwise applying pressure against the extension wire 140 within the cutout 121D, is intended to inhibit movement of the extension wire 140 with respect to the alignment device 120 during attachment of the extension wire 140 to the proximal end 40B of the guidewire 40. The anti-migration feature 180, in some examples, is not intended to inhibit removal of the extension wire 140 from within the extension holder 160 and the alignment device 120, for instance, once the extension wire 140 is attached to the guidewire 40 and it is desired to remove the extension wire 140 from within the extension holder 160 and the alignment device 120 (for instance, in order to perform a catheter exchange or some other such procedure for which the extension wire 140 is used). In some examples, the anti-migration feature 180 is configured to inhibit incidental movement of the extension wire 140 (for instance, from shaking, bumping, jostling, or the like during carrying, transportation, or shipping of the kit 100) but not overly restrain the extension wire 140 from being removed from within the extension holder 160 and the alignment device 120. For instance, in some examples, the anti-migration feature 180 provides a slight resistance to the extension wire 140 being removed from within the extension holder 160 and the alignment device 120 but does not provide enough resistance to cause the extension wire 140 to separate from the guidewire 40.

In some examples, the anti-migration feature 180 includes a resilient member 180 at least partially disposed within a portion of the lumen 122 of the body portion 121. With at least a portion of the extension wire 140 being disposed within the lumen 122, in some examples, the resilient member 180 contacts the extension wire 140 to inhibit movement of the extension wire 140 with respect to the alignment device 120. In further examples, the resilient member 180 frictionally inhibits incidental movement of the extension wire 140 with respect to the alignment device 120. In some examples, the anti-migration feature 180 includes a passage 130 within the body portion 121. In some examples, the passage 130 intersects with the lumen 122, and the resilient member 180 is positioned within the passage 130 and into the lumen 122 to contact the extension wire 140. In some examples, the passage 130 extends within the body portion 121 substantially perpendicularly to the lumen 122. In other examples, the passage 130 is at an angle other than ninety degrees to the lumen 122, provided it intersects or otherwise extends at least partially along or through the lumen 122. In some examples, the passage 130 extends completely through the body portion 121. In other examples, the passage 130 extends only partially through the body portion 121, for instance, through the sidewall 121C of the body portion 121 from the exterior of the body portion 121 to the lumen 122. In some examples, the resilient member 180 can be formed from one or more of silicone, Pebax, nylon, or the like.

Referring to FIGS. 4-7, there is shown a method of using the guidewire extension kit 100 to facilitate attachment of the extension wire 140 to the proximal end 40B of the guidewire or other working wire 40. In some examples, the guidewire 40 is partially disposed within a patient 10. In some examples, an introducer 20 is used to gain access to a location within the patient 10. For instance, in some examples, a small incision 12 is made and the introducer 20 is partially inserted within the incision 12 in order to access a desired location within the patient 10. A distal end of the guidewire 40, in some examples, is inserted into the introducer 20 and maneuvered to the desired location within the patient 10. Once the guidewire 40 is in place within the patient 10, in some examples, the introducer 20 can be removed from within the patient 10 and/or a catheter or other device can be at least partially inserted within the patient 10 over the guidewire 40. In some examples, once the distal end of the guidewire 40 is in place within the patient 10, it is desirable to maintain the distal end in the same position with little to no migration of the distal end of the guidewire 40 during the course of the procedure. During the course of the procedure, in some examples, it may be desirable to replace a catheter or otherwise switch devices over the guidewire 40. However, in some examples, an amount of the guidewire 40 extending from the patient 10 may be insufficient to execute a catheter switch or other such procedure. For instance, during a catheter exchange or other such procedure, a portion of the guidewire 40 should always be accessible to hold or otherwise constrain in order to inhibit migration of the distal end of the guidewire 40. Therefore, an overall length of working wire (either the guidewire 40 alone or the guidewire 40 coupled to the extension wire 140) extending from the patient 10 should be longer than the catheter to be exchanged, thereby enabling the physician or other user to hold or otherwise constrain the working wire either proximal or distal to the catheter at all times during the catheter exchange or other such procedure. In instances where the length of the guidewire 40 alone extending from the patient 10 is shorter than the catheter to be exchanged, then, in some examples, the extension wire 140 can be coupled to the proximal end 40B of the guidewire 40 to lengthen the length of the working wire extending from the patient 10 in order to enable a catheter exchange or other such procedure.

Figure 5:
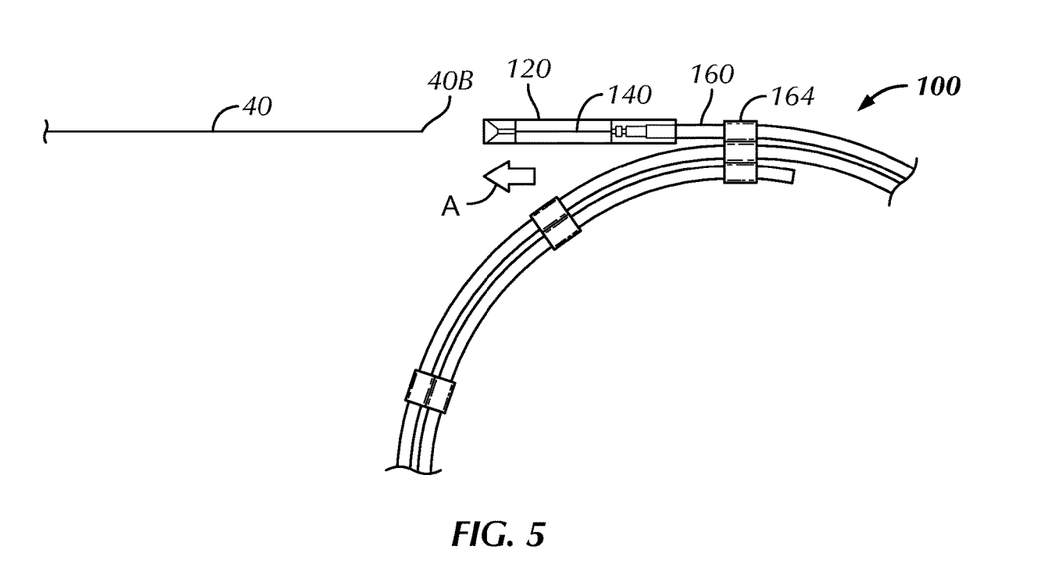
FIG. 5 shows an alignment device of a guidewire extension kit proximate the proximal end of the guidewire of FIG. 4.
Figure 6:
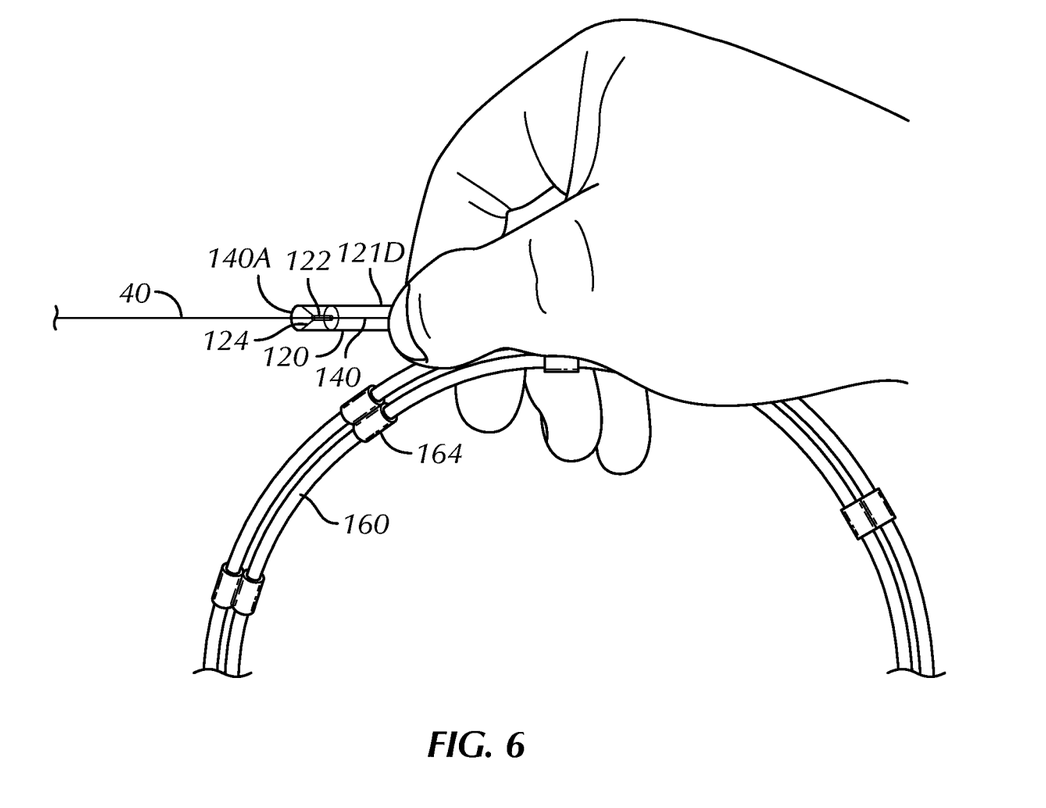
FIG. 6 shows attachment of an extension wire within the guidewire extension kit of FIG. 5 with the proximal end of the guidewire.
Figure 6A:
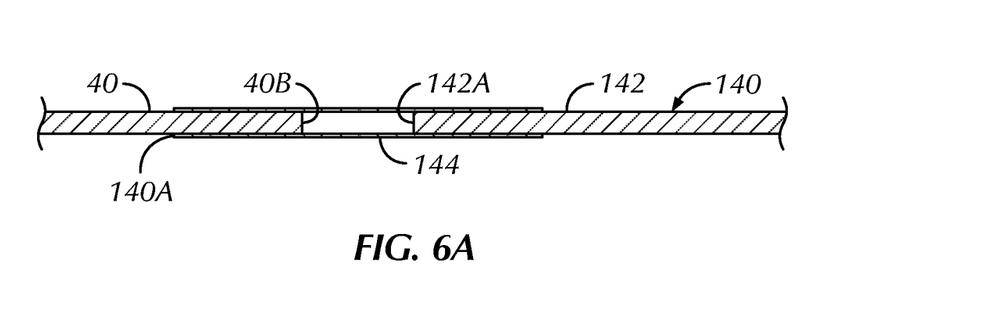
FIG. 6A is an enlarged view of the extension wire of FIG. 6 attached to the proximal end of the guidewire.

In some examples, a method of extending the guidewire 40 includes selecting the guidewire extension kit 100 for use in extending the guidewire 40. As described above, the guidewire extension kit 100, in some examples, should include an extension wire 140 that is sufficiently long to allow the physician or other user to constrain a portion of the extension wire 140 and/or the guidewire 40 during the catheter exchange or other procedure. Once the guidewire extension kit 100 is selected, in some examples, the alignment device 120 of the guidewire extension kit 100 is placed proximate to the proximal end 40B of the guidewire 40 to be extended, as shown in FIG. 5. The alignment device 120 of the guidewire extension kit 100, in some examples, can then be moved toward the proximal end 40B of the guidewire 40 (for instance, in the direction of arrow A). In some examples, the alignment device 120 can be moved toward the proximal end 40B of the guidewire 40 so that the proximal end 40B of the guidewire 40 enters the funnel portion 124 of the alignment device 120, becomes aligned with the distal end 140A of the extension wire 140, and attaches to the distal end 140A of the extension wire 140, as shown in FIGS. 6 and 6A. In some examples, a force can be exerted on a portion of the extension wire 140 within a portion of the lumen 122 exposed by the cutout 121D to press the extension wire 140 against the body portion 121 of the alignment device 120 to inhibit relative motion between the body portion 121 of the alignment device 120 and the extension wire 140 during attachment of the extension wire 140 to the guidewire 40. In some examples, the force can be exerted by placing one or more digits within the cutout 124 of the alignment device 120 to make contact with the portion of the extension wire 140 within the portion of the lumen 122 exposed by the cutout 124 and press the extension wire 140 against the body portion 121. For instance, in some examples, a thumb of the physician or other user can be used to exert the force against the portion of the extension wire 140 within the portion of the lumen 122 exposed by the cutout 124 to inhibit relative motion between the body portion 121 and the extension wire 140 during attachment of the extension wire 140 to the guidewire 40. In other examples, one or more other digits of the physician or other user can be used to exert the force against the portion of the extension wire 140. In still other examples, a clamp, clip, or other device can be used to insert within the cutout 124 in order to exert the force against the portion of the extension wire 140.

Figure 7:
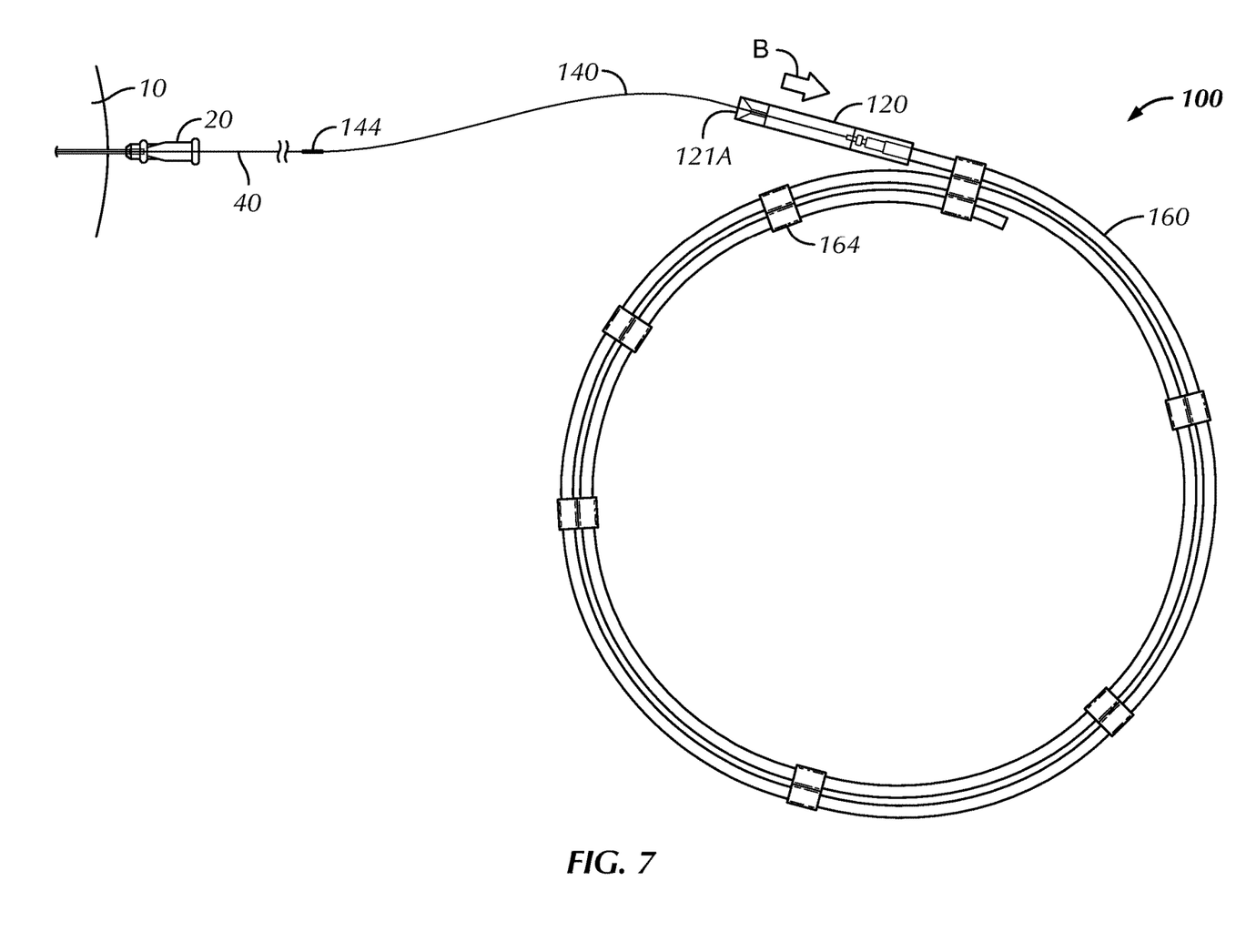
FIG. 7 shows partial removal of the alignment device and an extension holder from the extension wire of FIG. 6 attached to the guidewire.

Once the extension wire 140 is attached to the guidewire 40, in some examples, the force can be released on the portion of the extension wire 140 within the portion of the lumen 122 exposed by the cutout 124 to allow relative motion between the body portion 121 of the alignment device 120 and the extension wire 140. Once the extension wire 140 is attached to the guidewire 40, in some examples, the alignment device 120 can be pulled proximally (in the direction of arrow B) with respect to the guidewire 40, as shown in FIG. 7, to allow the extension wire 140 to be pulled from within and exit from the extension holder 160 and the distal end 121A of the body portion 121 of the alignment device 120, leaving the extension wire 140 connected to the guidewire 40, thereby extending the guidewire 40. In this way, the length of the working wire extending from the patient 10 (the combined lengths of the portion of the guidewire 40 extending from the patient 10 and the extension wire 140) can be made sufficient with which to exchange catheters or perform another procedure requiring a length of working wire longer than the length of the portion of the guidewire 40 extending from the patient 10.

The present inventor has recognized various advantages of the subject matter described herein. For instance, in some examples, the examples of systems, apparatuses, and methods described herein can be used to facilitate attachment of an extension wire to a guidewire or other working wire. The present inventor has recognized the present subject matter can be used to reduce the time and dexterity required to attach an extension wire to a guidewire or other working wire during a procedure, thereby potentially reducing time and expense for that procedure. While various advantages of the example apparatuses are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. An apparatus for extending a guidewire, the apparatus comprising:
   an extension wire including a distal end;
   an extension holder including an elongate interior, the extension holder being sized to house a majority of the extension wire within the interior of the extension holder prior to attachment to and use with the guidewire;
   a body portion including a sidewall and a lumen through the body portion, the lumen being sized to accommodate the distal end of the extension wire therein, the body portion being attached to the extension holder;
   a cutout defined within a portion of the sidewall of the body portion, the cutout extending through the sidewall from an exterior of the body portion to the lumen, the cutout allowing access to the lumen; and
   a funnel portion disposed within a distal end of the body portion, the funnel portion including an opening in the distal end of the body portion, the opening including an opening diameter larger than a lumen diameter of the lumen, the funnel portion including a tapered wall converging from the opening to the lumen, wherein, with the distal end of the extension wire disposed within the lumen, the funnel portion facilitates alignment and attachment of a proximal end of the guidewire with the distal end of the extension wire, the distal end of the extension wire including a connection member configured to couple to the proximal end of the guidewire, the connection member sized and shaped to accept the proximal end of the guidewire therein, such that, with the proximal end of the guidewire disposed within the connection member, the connection member exerts a retention force on the proximal end of the guidewire to retain the proximal end of the guidewire within the connection member and maintain coupling of the connection member to the proximal end of the guidewire, thereby maintaining coupling of the proximal end of the guidewire to the distal end of the extension wire.

2. The apparatus of claim 1, wherein the lumen is disposed along a longitudinal axis of the body portion.

3. The apparatus of claim 1, comprising an attachment portion disposed at a proximal end of the body portion, the attachment portion being configured for attachment to the extension holder.

4. The apparatus of claim 1, wherein, with the distal end of the extension wire disposed within the lumen of the body portion, a portion of the extension wire within the cutout is exposed, the cutout being sized to allow a user to contact the exposed portion of the extension wire to inhibit the extension wire from moving relative to the body portion during attachment of the extension wire to the guidewire.

5. The apparatus of claim 1, wherein the connection member includes a hypotube, the funnel portion being configured to direct the proximal end of the guidewire toward the hypotube disposed at the distal end of the extension wire to facilitate attachment of the proximal end of the guidewire within the hypotube.

6. The apparatus of claim 1, wherein the connection member includes a hypotube, the funnel portion being configured to direct the proximal end of the guidewire toward the hypotube disposed at the distal end of the extension wire to facilitate frictional engagement of the proximal end of the guidewire within the hypotube.

7. The apparatus of claim 1, comprising an anti-migration feature configured to inhibit movement of the extension wire with respect to the apparatus.

8. The apparatus of claim 7, wherein the anti-migration feature includes a resilient member at least partially disposed within a portion of the lumen of the body portion, wherein, with at least a portion of the extension wire being disposed within the lumen, the resilient member contacts the extension wire to inhibit movement of the extension wire with respect to the apparatus.

9. The apparatus of claim 8, wherein the anti-migration feature includes a passage within the body portion, the passage intersecting with the lumen, the resilient member being positioned within the passage and into the lumen to contact the extension wire.

10. A guidewire extension kit for facilitating attachment of an extension wire to a proximal end of a guidewire, the kit comprising:
    the extension wire configured to be attached to the proximal end of the guidewire, a distal end of the extension wire including a connection member configured to couple to the proximal end of the guidewire;
    an extension holder including an elongate interior, the extension holder being sized to house a majority of the extension wire within the interior of the extension holder prior to attachment to and use with the guidewire; and
    an alignment device coupled to a distal end of the extension holder, the alignment device including:
       a body portion including a sidewall and a lumen through the body portion, the lumen being sized to accommodate the distal end of the extension wire therein;
       a cutout defined within a portion of the sidewall of the body portion, the cutout extending through the sidewall from an exterior of the body portion to the lumen, the cutout allowing access to the lumen; and
       a funnel portion disposed within a distal end of the body portion, the funnel portion including an opening in the distal end of the body portion, the funnel portion including a tapered wall converging from the opening to the lumen, wherein, with the distal end of the extension wire disposed within the lumen, the funnel portion facilitates alignment and attachment of the proximal end of the guidewire with the connection member of the extension wire, the connection member being sized and shaped to accept the proximal end of the guidewire therein, such that, with the proximal end of the guidewire disposed within the connection member, the connection member exerts a retention force on the proximal end of the guidewire to retain the proximal end of the guidewire within the connection member and maintain coupling of the connection member to the proximal end of the guidewire, thereby maintaining coupling of the proximal end of the guidewire to the distal end of the extension wire.

11. The guidewire extension kit of claim 10, wherein the lumen is disposed along a longitudinal axis of the body portion.

12. The guidewire extension kit of claim 10, wherein the body portion includes an attachment portion disposed at a proximal end of the body portion, the attachment portion being configured for attachment to the extension holder.

13. The guidewire extension kit of claim 10, wherein, with the distal end of the extension wire disposed within the lumen of the body portion, a portion of the extension wire within the cutout is exposed, the cutout being sized to allow a user to contact the exposed portion of the extension wire to inhibit the extension wire from moving relative to the body portion during attachment of the extension wire to the guidewire.

14. The guidewire extension kit of claim 10, wherein the connection member includes a hypotube disposed at the distal end of the extension wire, the hypotube including a lumen sized to accept the proximal end of the guidewire to attach the extension wire to the guidewire.

15. The guidewire extension kit of claim 14, wherein the hypotube is configured to frictionally engage with the proximal end of the guidewire.

16. The guidewire extension kit of claim 10, wherein the alignment device includes an anti-migration feature to inhibit movement of the extension wire with respect to the alignment device.

17. The guidewire extension kit of claim 16, wherein the anti-migration feature includes a resilient member at least partially disposed within a portion of the lumen of the body portion, wherein, with at least a portion of the extension wire being disposed within the lumen, the resilient member contacts the extension wire to inhibit movement of the extension wire with respect to the alignment device.

18. The guidewire extension kit of claim 17, wherein the anti-migration feature includes a passage within the body portion, the passage intersecting with the lumen, the resilient member being positioned within the passage and into the lumen to contact the extension wire.

19. A method of extending a guidewire comprising:
selecting a guidewire extension kit for use in extending the guidewire, the guidewire extension kit including:
an extension wire configured to be attached to a proximal end of the guidewire;
an extension holder including an elongate interior, the extension holder being sized to house a majority of the extension wire within the interior of the extension holder prior to attachment to and use with the guidewire; and
an alignment device coupled to a distal end of the extension holder, the alignment device including:
a body portion including a sidewall and a lumen through the body portion, the lumen being sized to accommodate a distal end of the extension wire therein;
a cutout defined within a portion of the sidewall of the body portion, the cutout extending through the sidewall from an exterior of the body portion to the lumen, the cutout allowing access to the lumen; and
a funnel portion disposed within a distal end of the body portion, the funnel portion including an opening in the distal end of the body portion, the opening including an opening diameter larger than a lumen diameter of the lumen, the funnel portion including a tapered wall converging from the opening to the lumen, wherein, with the distal end of the extension wire disposed within the lumen, the funnel portion facilitates alignment and attachment of the proximal end of the guidewire with the distal end of the extension wire;
placing the alignment device of the guidewire extension kit proximate to the proximal end of the guidewire to be extended;
exerting a force on a portion of the extension wire within a portion of the lumen exposed by the cutout to press the extension wire against the body portion of the alignment device to inhibit relative motion between the body portion of the alignment device and the extension wire;
moving the alignment device toward the proximal end of the guidewire so that the proximal end of the guidewire enters the funnel portion of the alignment device, becomes aligned with the distal end of the extension wire, and attaches to the distal end of the extension wire;
releasing the force on the portion of the extension wire within the portion of the lumen exposed by the cutout to allow relative motion between the body portion of the alignment device and the extension wire; and
pulling the alignment device proximally with respect to the guidewire to allow the extension wire to exit from the extension holder and the distal end of the body portion of the alignment device, leaving the extension wire connected to the guidewire, thereby extending the guidewire.

20. The method of claim 19, wherein exerting the force on the portion of the extension wire within the portion of the lumen exposed by the cutout includes placing one or more digits within the cutout of the alignment device to make contact with the portion of the extension wire within the portion of the lumen exposed by the cutout.

\* \* \* \* \*